US00PP20752P3

(12) United States Plant Patent
Gooch

(10) Patent No.: US PP20,752 P3
(45) Date of Patent: Feb. 16, 2010

(54) CHERRY TREE NAMED 'MADDISON'

(50) Latin Name: *Prunus avium*
Varietal Denomination: Maddison

(75) Inventor: Ed Gooch, Malaga, WA (US)

(73) Assignee: Synder, LLC, Wenatchee, WA (US)

( * ) Notice: Subject to any disclaimer, the term of this patent is extended or adjusted under 35 U.S.C. 154(b) by 8 days.

(21) Appl. No.: 11/999,960

(22) Filed: Dec. 7, 2007

(65) Prior Publication Data

US 2009/0151031 P1 Jun. 11, 2009

(51) Int. Cl.
*A01H 5/00* (2006.01)

(52) U.S. Cl. ..... Plt./181

(58) Field of Classification Search ..... Plt./181
See application file for complete search history.

*Primary Examiner*—Kent L Bell

(57) ABSTRACT

'Maddison' is a new and distinct cherry tree notable for its early ripening, large size, and dark color as compared to 'Bing.'

3 Drawing Sheets

Genus and species: *Prunus avium.*
Variety denomination: 'Maddison'.

BACKGROUND AND SUMMARY OF THE VARIETY

The new cherry variety 'Maddison' originated as a naturally occurring whole tree mutation of 'Bing' (not patented). The mutation was discovered as a seedling in a commercial orchard near Malaga, Washington, in 2004, and was distinguishable from 'Bing' by its early ripening, large size, and dark color. Trees were propagated from the seedline by chin budding onto 'Mazzard' rootstock to determine whether the desirable characteristics would carry through to asexually propagated progeny. It has been found that the characteristics of early ripening, large size, and dark color, as well as other characteristics of the tree and its fruit, were reproduced through asexual propagation and have remained stable through successive generations.

'Maddison' is a new and distinct cherry tree notable for its early ripening, large size, and dark color as compared to 'Bing.'

BRIEF DESCRIPTION OF THE PHOTOGRAPHS

Figure 1:
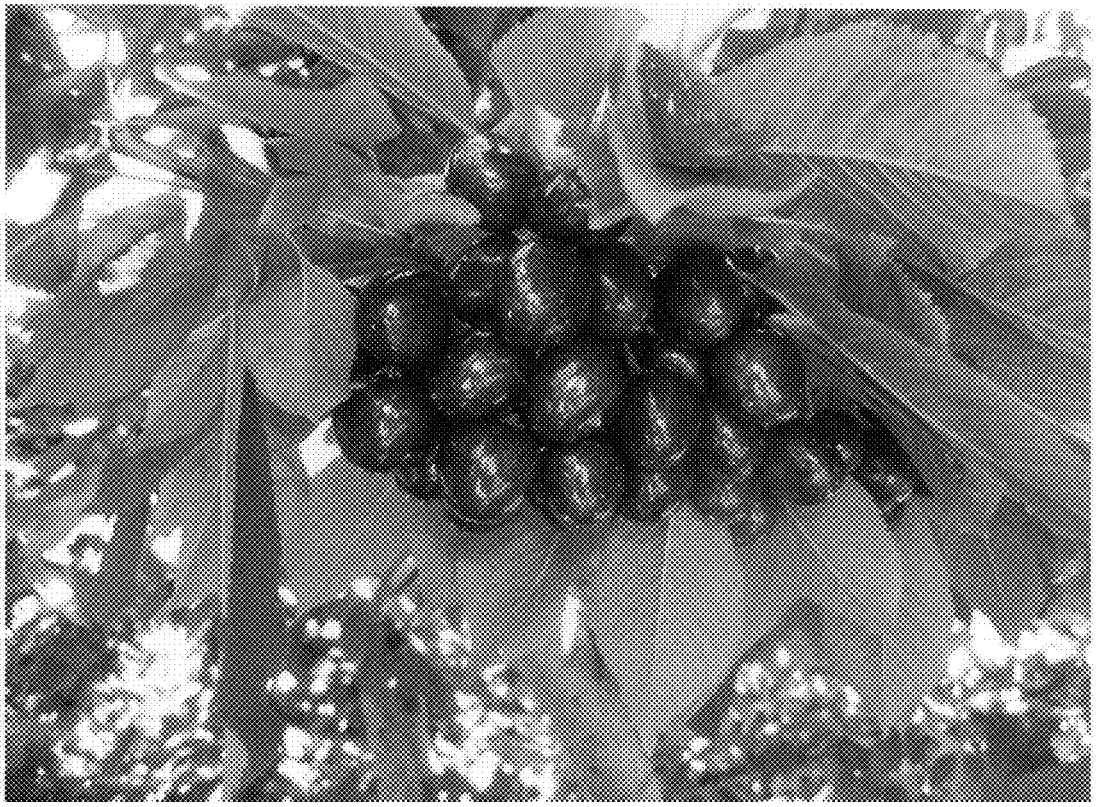
Figure 2:
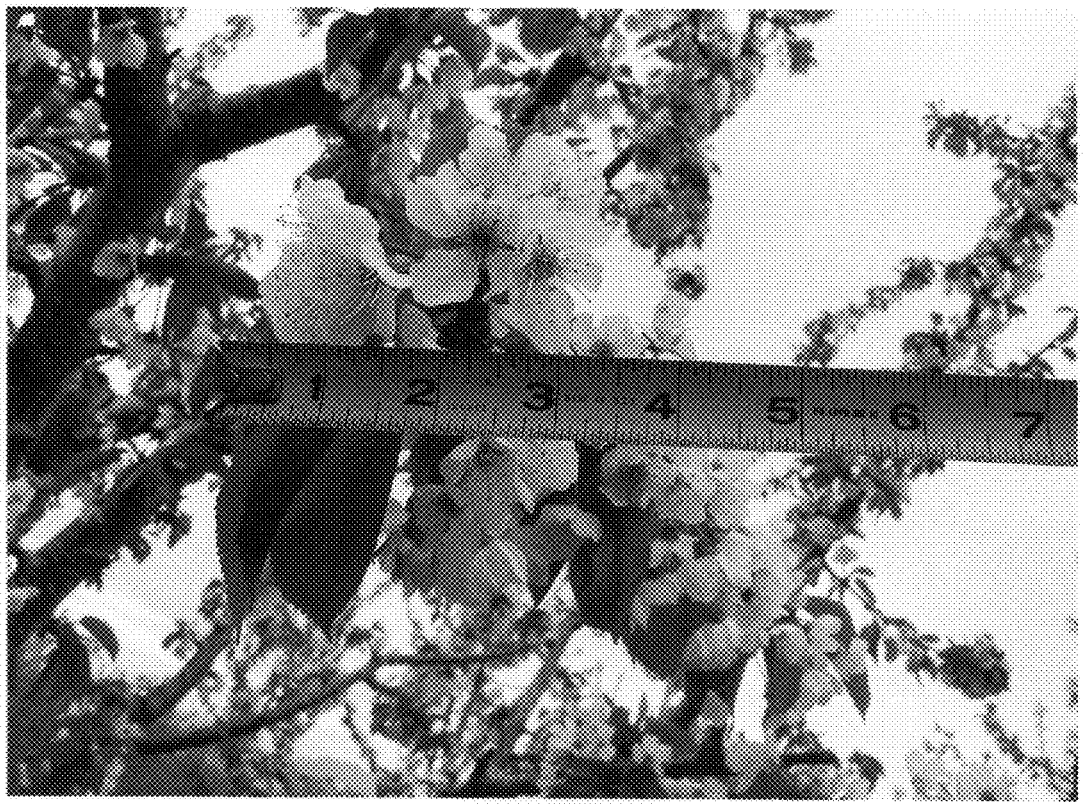
Figure 3:
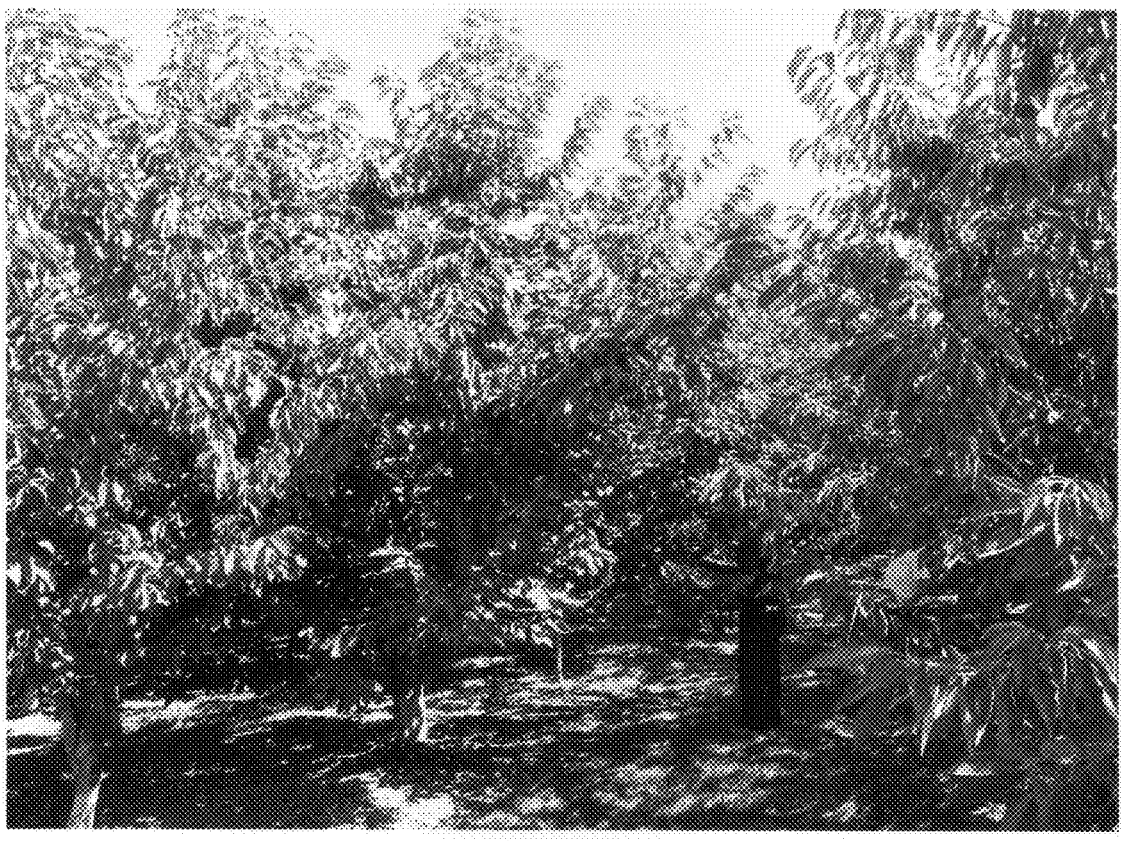

FIG. 1 shows the fruit and leaves of the new variety;
FIG. 2 shows the blossoms of the new variety; and
FIG. 3 shows the tree of the new variety.

The colors of this illustration may vary with lighting conditions. Color characteristics of this new variety should therefore be determined with reference to the observations described herein, rather than from these illustrations alone.

DETAILED BOTANICAL DESCRIPTION

The following detailed botanical description is based on observations of the nine-year-old originally discovered tree, made during the 2007 growing season at Malaga, Washington. It should be understood that the characteristics described will vary somewhat depending upon cultural practices and climatic conditions, and can vary with location and season.

Color descriptions are made with reference to The Royal Horticulture Society Colour Chart. Quantified measurements are expressed as an average of measurements taken from a number of individual plants of the new variety. The measurements of any individual plant, or any group of plants, of the new variety may vary from the stated average.

Tree:

*Size Height.*—5 m, spread 4.4 m.
*Vigor.*—Vigorous, about 70 cm per year.
*Branching habit.*—Spreading to upright.
*Density.*—Dense.
*Hardiness.*—Hardy in area tested (USDA Hardiness Zone 6A).
*Productivity.*—95 kg (2007 growing season).
*Bearing.*—Annual.
*Trunk Diameter.*—22.8 cm at 15 cm above soil; Bark somewhat rough on old wood, smoother on new wood, gray 201D; Trunk lenticel width 2 mm, length varies, orange-white 159A.
*Branch.*—Diameter 4 cm at 150 cm from trunk, length 1.4 m, crotch angle 20° to 30°, texture smooth, greyed-orange 175A, branch lenticel width 2 mm, length varies, quantity 6 per square inch.

Leaves:

*Size.*—Length 18.4 cm, width 8.2 cm, thickness 0.4 mm.
*Shape.*—Elliptic, base equilateral, apex acuminate, recurved inward.
*Texture.*—Glabrous.
*Margin.*—Serrate to serrulate.
*Color.*—Upper surface green 1 37A, lower surface green 137D.
*Midvein.*—Width 3 mm, upper surface yellow-green 145C, lower surface green 142C.
*Petiole.*—Length 44 mm, diameter 1.5 mm; upper surface yellow-green 146C, lower surface green 142C.
*Glands.*—Quantity 2 per leaf, oval; length 3 mm, width 2 mm, yellow-green 146C.

Flowers:

*Buds.*—Quantity 10 per spur; length 1.3 cm, width 0.5 cm; elongated, cylindrical;yellow-green N144D.

*Bloom Date.*—First bloom April 6; fill bloom date Apr. 13, (2007 growing season, Malaga, Washington); first bloom April 13, full bloom Apr. 20, (2009 growing season, Malaga, Washington).

*Diameter of open flower.*—3.3 cm.

*Relative position of petal margin.*—Slightly overlapping.

*Petals.*—Quantity 5 per flower; shape round, concave; length 1.5 cm, width 1.5 cm; apex retuse, base equilateral, margin slightly undulated; upper surface white 155D, lower surface white 155D.

*Pistils.*—Quantity 1 per flower; length 9 mm, oblong; yellow green 149C; ovary elongated, length 1 to 2 mm; style 8 mm, yellow green 149C.

*Stamen.*—Quantity 25 to 27 per flower; length 9 mm; white 155D; pollen abundant, yellow orange 17B.

*Sepals.*—Quantity 5; length 0.8 cm, width 0.6 cm; lanceolate, curled, apex rounded, base equilateral, margin smooth, surface smooth; green 138B with greyed red 181A along margin.

*Pollination requirements.*—Not self fertile, pollinator required; not compatible with 'Bing'.

Fruit:

*Size.*—Apical diameter 28 mm, axial diameter 25 mm; 6.2 g to 9.2 g.

*Shape.*—Heart shaped, symmetrical; apex acuminate, base flat with slight shoulder.

*Suture.*—Very shallow.

*Stem.*—Length 4.4 cm, diameter 2 mm; green 142C.

*Cavity.*—Depth 4 mm, diameter 9 mm.

*Skin.*—Thickness 0.5 mm, smooth, glabrous, glossy, tenacious to flesh, no tendency to crack noted; red purple 59A.

*Flesh.*—Firm, dense, juicy; red purple 59A.

*Juice.*—Abundant.

*Aroma.*—Rich.

*Sugar content.*—16.1 Brix to 21.6 Brix.

*Stone.*—Length 13 mm, width 7 mm; oval, with rounded acuminate apex and obtuse base; texture smooth, glabrous; flesh not tenacious to stone; no tendency to split observed; color greyed-orange 163D.

*Kernel.*—Length 8 mm, width 5 mm, thickness 4 mm; shape ovate, with rounded acuminate apex and rounded obtuse base, color yellow white 158A with greyed purple 184C tip; taste highly astringent with almond essence; plump and firm with good viability.

Diseases/pests: Possibly resistant to mildew; very minor susceptibility to doubling.

Market use: High quality early market fruit.

Keeping quality: Excellent; 2 months under refrigeration with no apparent pitting or wrinkling.

Shipping quality: Excellent; no apparent bruising.

Maturity date: Eating ripe on June 20; date of first and last picking Jun. 20, (2007 growing season, Malaga, Washington).

Claim:

1. What is claimed is a new and distinct cherry tree as shown and described herein.

* * * * *

UNITED STATES PATENT AND TRADEMARK OFFICE

CERTIFICATE OF CORRECTION

PATENT NO. : PP 20,752 P3
APPLICATION NO. : 11/999960
DATED : February 16, 2010
INVENTOR(S) : Ed Gooch It is certified that error appears in the above-identified patent and that said Letters Patent is hereby corrected as shown below:

At column 1, line 12, "seedline by chin" should read --seedling by chip--
At column 2, line 8, "Size Height. 5 m" should read --Size. - Height 5 m--
At column 2, line 16, "Trunk Diameter. 22.8 cm" should read --Trunk. - Diameter 22.8 cm--
At column 3, line 1, "fill bloom date" should read --full bloom date--

Signed and Sealed this

Sixth Day of April, 2010

David J. Kappos

David J. Kappos
*Director of the United States Patent and Trademark Office*